United States Patent
Gold et al.

(10) Patent No.: US 6,319,892 B1
(45) Date of Patent: Nov. 20, 2001

(54) USE OF RECOMBINANT MYELIN PROTEIN FOR TREATING T-CELL-MEDIATED AUTOIMMUNE DISEASES OF THE PERIPHERAL NERVOUS SYSTEM

(76) Inventors: Ralf Gold; Andreas Weishaupt, both of Neurologisch Klinik und Polyklinik im Kopfklinikum, Josef-Schneider-Strasse 11, Wurzburg (DE), D-97080

( * ) Notice: Subject to any disclaimer, the term of this patent is extended or adjusted under 35 U.S.C. 154(b) by 0 days.

(21) Appl. No.: 09/214,943

(22) PCT Filed: Jul. 18, 1997

(86) PCT No.: PCT/DE97/01535

§ 371 Date: Mar. 15, 1999

§ 102(e) Date: Mar. 15, 1999

(87) PCT Pub. No.: WO98/03647

PCT Pub. Date: Jan. 29, 1998

(51) Int. Cl.⁷ ................................................ C02K 14/00
(52) U.S. Cl. ................................ 514/2; 530/350; 530/300
(58) Field of Search ............................... 514/6, 8, 12, 21, 514/13, 14; 530/326, 300, 350

Primary Examiner—Karen Cochrane Carlson
(74) Attorney, Agent, or Firm—Fulbright & Jaworski, LLP

(57) ABSTRACT

The present invention relates to the use of recombinant myelin protein for treating T cell-mediated autoimmune diseases of the peripheral nervous system.

6 Claims, 4 Drawing Sheets

Figure 1:
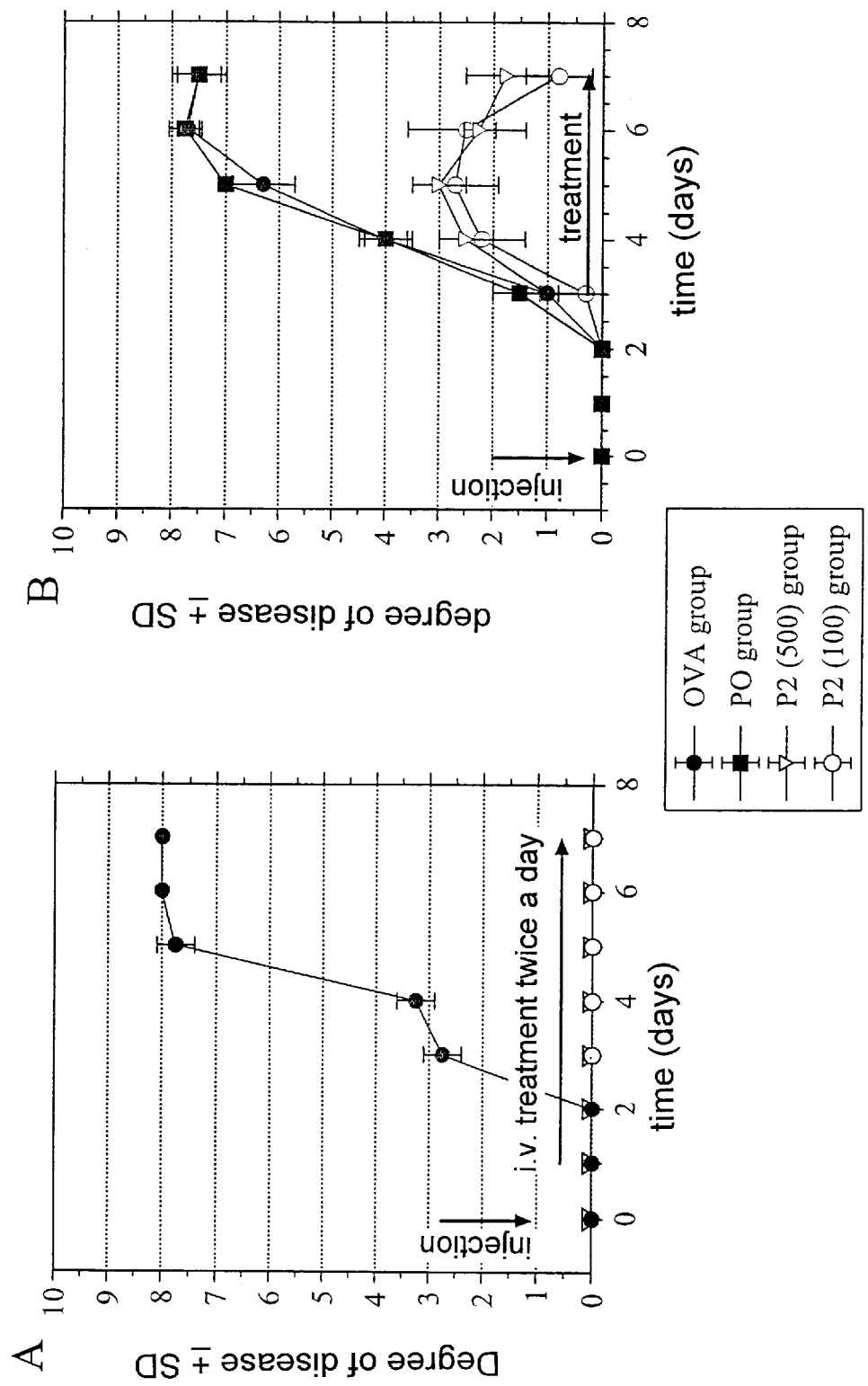

```
  1     M     S     N     K     F     L     G     T     W     K     L     V     S     S     E     N      16
  1    ATG   AGC   AAC   AAA   TTC   CTG   GGC   ACC   TGG   AAA   CTT   GTC   TCT   AGC   GAG   AAC     48
       NdeI
                         E
 17     F     D     D     Y     M     K     A     L     G     V     G     L     A     T     R     K      32
 49    TTT   GAC   GAT   TAC   ATG   AAA   GCT   CTG   GGT   GTG   GGG   TTA   GCC   ACC   AGA   AAA     96
                                           P
 33     L     G     N     L     A     K     P     T     V     I     I     S     K     K     G     D      48
 97    CTG   GGA   AAT   TTG   GCC   AAA   CCC   ACT   GTG   ATC   ATC   AGC   AAG   AAA   GGA   GAT    144
                                           P
 49     I     I     T     I     R     T     E     S     T     F     K     N     T     E     I     S      64
145    AAT   ATA   ACT   ATA   CGA   ACT   GAA   AGT   ACC   TTT   AAA   AAT   ACA   GAA   ATC   TCC    192

65     F     K     L     G     Q     E     F     E     E     T     T     A     D     N     R     K      80
193    TTC   AAG   CTA   GGC   CAG   GAA   TTT   GAA   GAA   ACC   ACA   GCT   GAC   AAT   AGA   AAG    240
                         T                       A
 81     T     K     S     I     V     T     L     Q     R     G     S     L     N     Q     V     Q      96
241    ACC   AAG   AGC   ATC   GTA   ACC   CTG   CAG   AGA   GGA   TCA   CTG   AAT   CAA   GTG   CAG    288
             K                 N
 97     R     W     D     G     K     E     T     T     I     K     R     K     L     V     N     G     112
289    AGA   TGG   GAT   GGC   AAA   GAG   ACA   ACC   ATA   AAG   AGA   AAG   CTA   GTG   AAT   GGG    336
                         V                                   D
113     K     M     V     A     E     C     K     M     K     G     V     V     C     T     R     I     128
337    AAA   ATG   GTA   GCG   GAA   TGT   AAA   ATG   AAG   GGC   GTG   GTG   TGC   ACC   AGA   ATC    384

129     Y     D     V     H     H     H     H     H     *                                                136
385    TAT   GAC   GTC   CAT   CAT   CAC   CAC   CAT   TAG                                               408
             AatII
```

Fig. 4

USE OF RECOMBINANT MYELIN PROTEIN FOR TREATING T-CELL-MEDIATED AUTOIMMUNE DISEASES OF THE PERIPHERAL NERVOUS SYSTEM

This application is a national stage application PCT/D697/01535, filed Jul. 18, 1997.

This invention relates to the use of recombinant myelin protein for treating T cell-mediated autoimmune diseases of the peripheral nervous system.

Neuropathies of autoimmune genesis have been treated by immunosuppressive or immunomodulating therapy so far. Common treatment methods are the administration of steroids (e.g. cortisone), immunoglobulins and long-term immunosuppressive agents (e.g. azathiopine) or the conduction of plasmapheresis. However, many undesired side-effects accompany these measures as drawbacks, and success is often insufficient.

Therefore, it is the object of the present invention to provide a successful and careful method for treating T cell-mediated autoimmune diseases of the peripheral nervous system.

The inventors have found that autoimmune-B cell and autoimmune-T cell responses, which are directed against peripheral myelin components, play an important part in the pathogenesis of inflammatory demyelinating diseases of the nervous system. These diseases are known as immunoneuropathies of the peripheral nervous system, e.g. chronic inflammatory polyneuritis, Guillain-Barré syndrome, vasculitides of the peripheral nervous system and neuritides in the case of gammopathies.

The presence of neuritic molecules in myelin was proved for the first time by the induction of experimental autoimmune neuritis (EAN) in an animal model where rodents were immunized with homogenates of peripheral nerve tissue (Waksman et al., J. Exp. Med. 102, 213–235 (1955)) or purified P2 protein (Brostoff et al., Nature (New Biol.) 235, 210–217 (1972)). In this animal model for disease of the peripheral nervous system, the immune system is disregulated and autoaggressive T lymphocytes are produced which are specific for structural proteins of the myelin of the peripheral nervous system and result in demyelinization and in inflammation in the peripheral nervous system. This animal model stands in place for the above-mentioned autoimmune diseases of the peripheral nervous system in which an increased T cell number, demyelinization and neuritides occur as well.

The inventors have now found that these T cell-mediated autoimmune diseases of the peripheral nervous system can be eliminated and at least be improved, respectively, by the administration of high doses of the autoantigen, i.e. by the high-dosed administration of myelin protein. This treatment is named high-dosed antigen treatment and results in gentle death of the T cells (T cell apoptosis) which in the final analysis are responsible for the induction and course of the disease. In this connection, it proved to be particularly suitable to carry out the high-dosed antigen treatment in an early disease stage. However, also in the case of an advanced clinical picture considerable success can still be achieved. Thus, it has proved efficient to administer the antigen (myelin protein) in doses of 100 to 500 μg in rats. For man, higher doses which can easily be determined by a person skilled in the art must be applied in accordance with the greater body weight. For example, a daily dose of from about 5–50 mg, more preferably from about 10 mg–30 mg is exemplary of doses for humans. Intravenous injection is particularly preferred.

All presently known myelin proteins, such as PO, peripheral myelin glycolipids (e.g. GM1), MBP, PLP, MOG, MAG, S-100 protein and particularly P2, are suited as autoantigen to be administered. According to the invention the term "myelin protein" includes mixtures of various proteins, protein fragments and mixtures of protein fragments. It has to be emphasized that these proteins should have been produced recombinantly, since it is very expensive and time-consuming to purify a sufficient amount of proteins from natural myelin. Moreover, when purified protein from bovine nerve myelin is used, BSE can easily be transmitted. In addition, the response in man to purified bovine protein differs very strongly from that to human P2, since some amino acid differences exist between the human sequence and the bovine one. Therefore, natural human P2 has been used for T cell experiments so far, since recombinant protein was not yet available. However, it has been produced meanwhile and it is particularly preferred according to the invention to use recombinant human P2 protein. The sequence and isolation of this protein is described in "Weishaupt et al., J. of Neuroimmunology 63, 149–156 (1995 which is incorporated by reference)". The sequence shown in this publication is illustrated in FIG. 4. Further recombinant myelin proteins are described in Oettinger et al., J. of Neuroimmunology 44, 157–163 (1993 which is incorporated by reference).

The invention is now further described by the figures showing:

FIGS. 1A+B: treatment of EAN with differing doses of rhP2.

Figure 2:
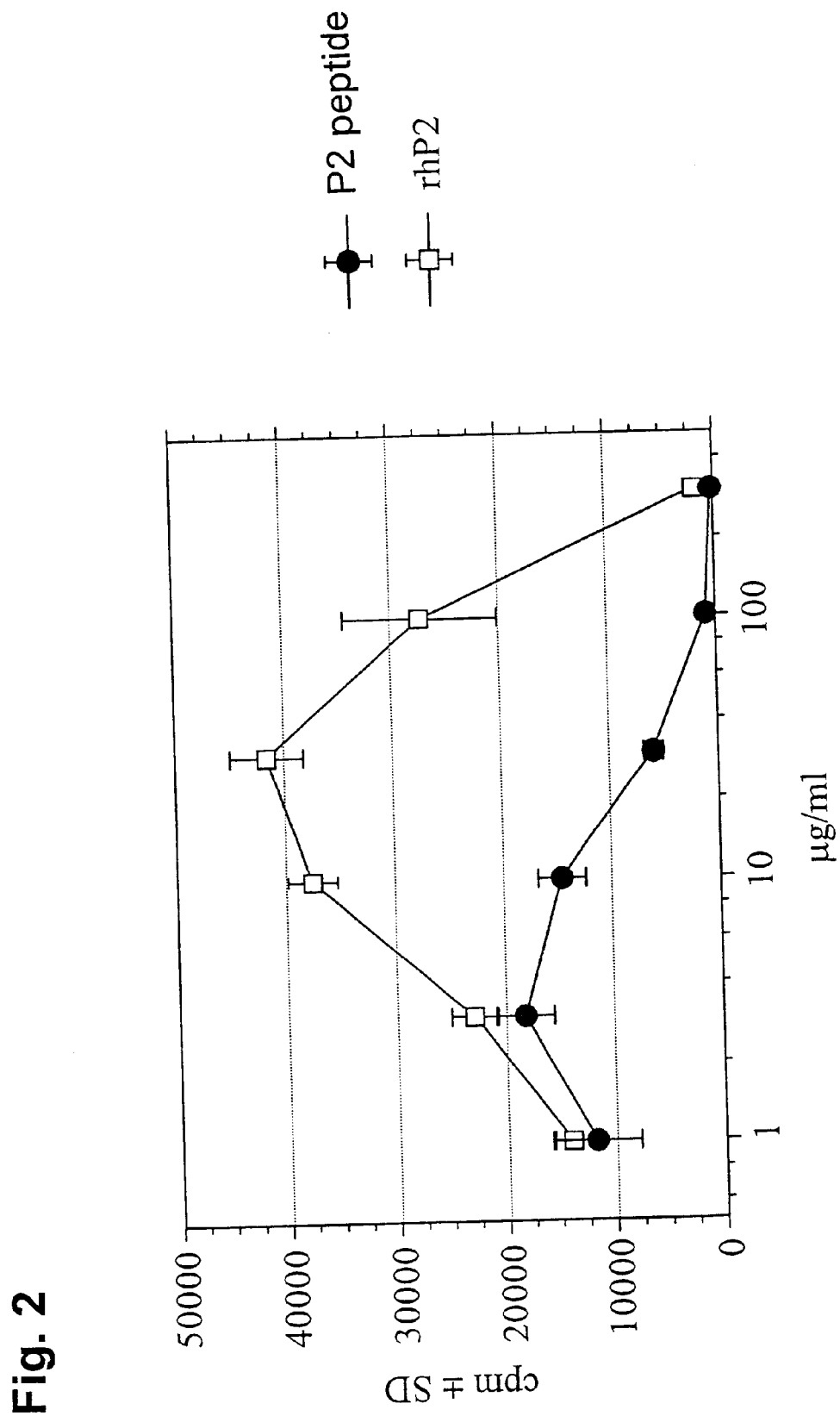

FIG. 2: suppression of a rat T cell line by high-dosed antigen administration.

Figure 3:
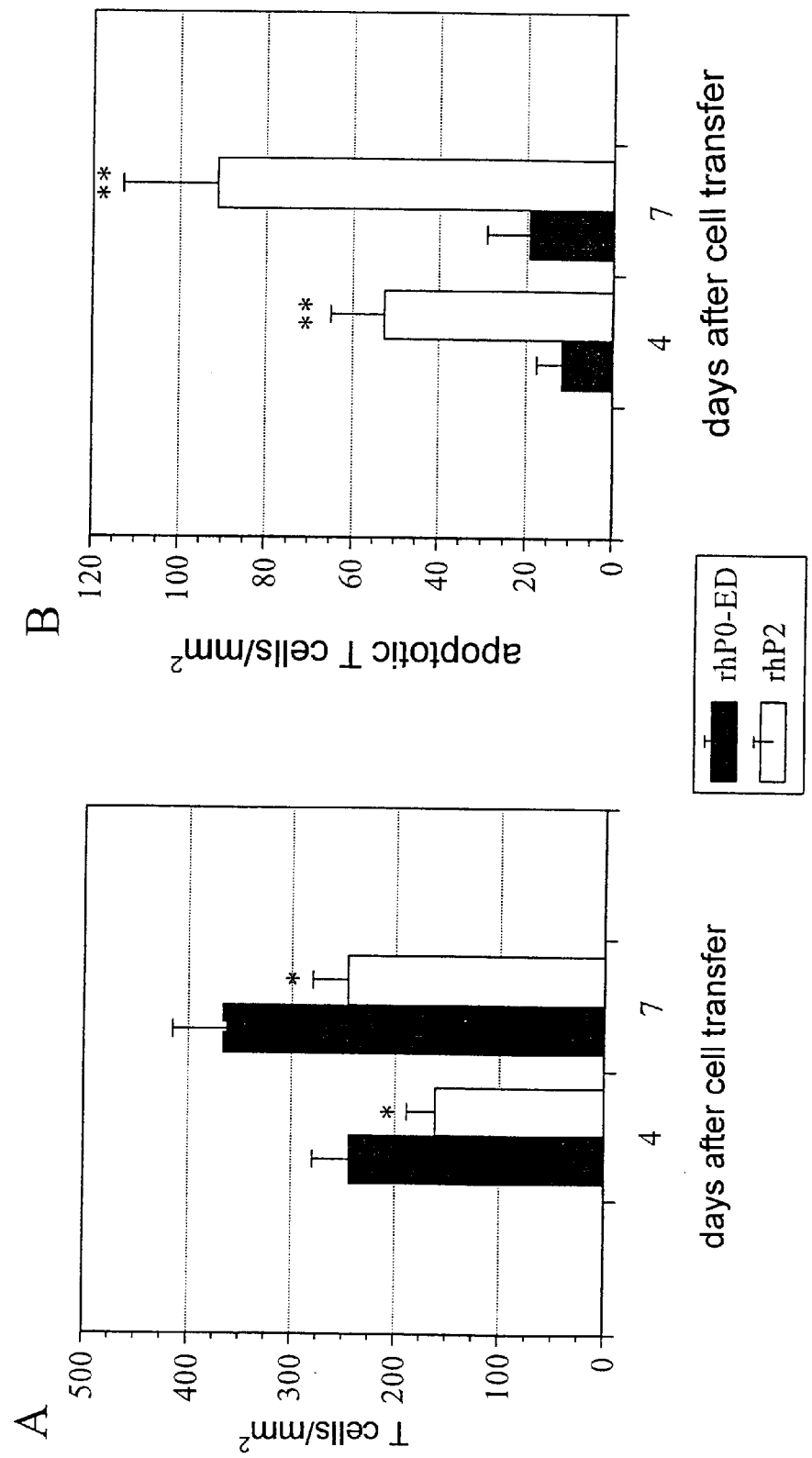

FIG. 3A: immunocytochemical analysis of the T cell infiltration in rhP2-treated rats and rhP0 control animals when EAN is present. The values are given as mean density of T cells/mm$^2$±standard deviation from 3 animals/group.

FIG. 3B: T cell apoptosis in treated animals as compared to spontaneous T cell apoptosis in control animals. The values are given as mean density of apoptotic cells/mm$^2$±standard deviation from 3 animals/group.

FIG. 4: Nucleotide sequence and corresponding amino acid sequence of the human recombinant (complete sequence) and bovine P2 protein (only the amino acid exchanges are indicated). Introduced enzyme restriction sites and histidine tail sequences are underlined.

The invention is now described in more detail by means of the examples.

EXAMPLES

Female Lewis rats (age: 6–8 weeks; weight: 125–160 g) were used.

Complete recombinant human P2 protein (rhP2) and the extracellular domain of recombinant human P0 protein (rhP0) were expressed in *E. coli* as described in "Weishaupt et al., J. of Neuroimmunology 63, 149–156 (1995)" and purified by Ni$^{2+}$-NTA affinity chromatography and gel filtration chromatography.

Neuritic P2-specific T cell lines G5 and G7 were produced as described in "Linington et al., J. Immunol. 133, 1946–1950 (1984)".

Example 1

In a first experiment, several rats were given 500 μg rhP2 and 100 μg rhP2, respectively, twice a day for 7 days, 8×10$^6$ activated P2-specific T cells being transmitted on day 0 as well, which should be capable of causing EAN. However, no symptoms occurred in the animals by day 24 (end of experiment). In contrast thereto, the rats of the control group which had received ovalbumin instead of rhP2 showed the typical disease process of EAN, a paraplegia and tetraparesis maximum of the disease being observed on day 6 after the T cell injection. The results are shown in FIG. 1A.

Example 2

The rats which had been given $8\times10^6$ P2-specific T cells by injection were divided into differing groups 3 days after the T cell injection:

Group 1 received 500 µg rhP2 twice a day, group 2 received 100 µg rhP0 twice a day, group 3 received 100 µg rhP2 twice a day, group 4 received 500 µg ovalbumin twice a day.

Rats which had been treated with either 500 µg or 100 µg rhP2 (groups 1 and 3) twice a day, developed only mild symptoms with a maximum on day 5 after the cell injection. On day 6, the symptoms in rhP2-treated groups 1 and 3 began to decrease. Since P2-specific T cells had been injected to trigger EAN, the administration of P0 protein could yield no positive effect, as expected. The results are shown in FIG. 1B.

Table 1, presented infra shows that the histological analysis of the sciatic nerve showed a strong inflammatory reaction with strong infiltration of T cells and macrophages in groups 2 and 4 (rhP0 group and ovalbumin group). Only few infiltrates were found in rhP2-treated groups 1 and 3.

| | number of rats | duration of treatment [days after the immunization] | disease degree ± SD at maximum | T cell infiltrates at maximum T cells/mm² [average ± SD] | macrophages infiltrates at maximum macrophages/mm² [average ± SD] |
|---|---|---|---|---|---|
| Early disease [treatment per day] | | | | | |
| 2x 500 µg Ovalbumin (ova) | 2 | 1–7 | 7.75 ± 0.3 | 248.7 ± 21.5 | 113.2 ± 17.8 |
| 1x 100 µg rhP2 + 1x ova | 2 | 1–7 | 0 | 21.5 ± 5.8* | 13.1 ± 5.2* |
| 2x 100 µg rhP2 | 2 | 1–7 | 0 | 13.7 ± 4.1* | 9.2 ± 3.2* |
| 1x 500 µg rhP2 + 1x ova | 2 | 1–7 | 0 | 13.5 ± 4.8* | 8.5 ± 2.8* |
| 2x 500 µg rhP2 | 2 | 1–7 | 0 | 6.3 ± 2.7* | 3.2 ± 2.2* |
| Advanced disease [treatment per day] | | | | | |
| 2x 500 µg Ovalbumin | 3 | 3–7 | 7.7 ± 0.2 | 258.7 ± 38.1 | 100.4 ± 38.8 |
| 2x 500 µg rhP0 | 3 | 3–7 | 7.75 ± 0.3 | 249.2 ± 26.7 | 95.7 ± 19.1 |
| 2x 100 µg rhP2 | 3 | 3–7 | 3.0 ± 0.5** | 37.6 ± 12.2* | 16.1 ± 7.2* |
| 2x 500 µg rhP2 | 3 | 3–7 | 2.7 ± 0.8** | 6.5 ± 2.8* | 2.2 ± 1.7* |

\* = p < 0.01 vs. Ovalbumin,
\*\*p < 0.05 vs. Ovalbumin.

Example 3

T cells were incubated with increasing doses of rhP2 or the neuritic P2 peptide (amino acids 53–78). For this purpose, $1.5\times10^4$ responder G5 or G7 T cells, $7.5\times10^5$ irradiated (3000 rad) thymocytes and various concentrations of rhP2 or the neuritic P2 peptide in a total volume of 100 µl per well were added to a 96-well microtiter plate. After 48 hours, the cells were labeled with 0.2 µCi/well $^3$H-dT for 16 hours and harvested at the indicated time. The cells were collected on a glass fiber filter paper and the radioactivity distribution was evaluated. The results are shown in FIG. 2. It follows therefrom that the proliferation of the neuritic T cells was at a maximum with 3 µg/ml of the neuritic P2 peptide and with 30 µg/ml of the rhP2 protein and then dropped constantly with higher concentrations.

Example 4

On day 3 or 6 after an intravenous injection of $8\times10^6$ activated P2-specific T cells, Lewis rats were given 500 µg rhP2 or 500 µg of the control antigen rhP0, which was repeated after 12 hours. 6 hours after the last injection, the animals were killed and the sciatic nerve was removed. The histological analysis of the sciatic nerve of rhP2 recipients showed a reduction of the inflammatory infiltrates by about 30% as compared to the rhP0 controls. From a morphological point of view, the T cells showed typical signs of apoptosis. The results are summarized in FIGS. 3A+B.

What is claimed is:

1. A method for treating T cell mediated autoimmune peripheral nervous system disease, comprising administering to a subject in need thereof a sufficient amount of at least one recombinant myelin protein to alleviate said T cell mediated autoimmune peripheral nervous system disease.

2. The method of claim 1, wherein said recombinant myelin protein is P2, P0, myelin basic protein (MBP), proteolipid protein (PLP), myelin oligodentrocyte glycoprotein (MOG), myelin associated glycoprotein (MAG), or s-100 protein.

3. The method of claim 1, comprising administering a mixture of recombinant myelin proteins.

4. The method of claim 1, wherein said T cell mediated autoimmune peripheral nervous system disease is chronic inflammatory polyneuritis, Guillaine-Barré syndrome, peripheral nervous system vasculitides, or gammopathy related neuritides.

5. The method of claim 1, comprising administering said recombinant protein in the form of a high-dosed antigen treatment.

6. A method for making a composition for treating a T cell mediated autoimmune disease, comprising admixing at least one recombinant myelin protein and a pharmaceutically acceptable carrier.

\* \* \* \* \*